United States Patent
Bertolini et al.

(10) Patent No.: US 11,498,917 B2
(45) Date of Patent: Nov. 15, 2022

(54) PROCESS FOR THE PREPARATION OF LIFITEGRAST

(71) Applicant: OLON S.P.A., Rodano (IT)

(72) Inventors: Giorgio Bertolini, Rodano (IT); Lazzaro Feliciani, Casaletto Lodigiano (IT); Davide Longoni, Rodano (IT); Mara Sada, Segrate (IT); Matteo Valli, Rodano (IT)

(73) Assignee: OLON S.P.A., Rodano (IT)

( * ) Notice: Subject to any disclaimer, the term of this patent is extended or adjusted under 35 U.S.C. 154(b) by 0 days.

(21) Appl. No.: 16/972,856

(22) PCT Filed: Jun. 13, 2019

(86) PCT No.: PCT/IB2019/054943
§ 371 (c)(1),
(2) Date: Dec. 7, 2020

(87) PCT Pub. No.: WO2019/239364
PCT Pub. Date: Dec. 19, 2019

(65) Prior Publication Data
US 2021/0246123 A1    Aug. 12, 2021

(30) Foreign Application Priority Data

Jun. 14, 2018   (IT) .................. 102018000006337

(51) Int. Cl.
*C07D 405/06*   (2006.01)
(52) U.S. Cl.
CPC .................. *C07D 405/06* (2013.01)
(58) Field of Classification Search
CPC . C07D 406/06; C07D 405/06; A61K 31/4709
(Continued)

(56) References Cited

U.S. PATENT DOCUMENTS 8,367,701 B2 * 2/2013 Burnier .................. A61P 17/14
514/307

FOREIGN PATENT DOCUMENTS

WO    2005044817 A1   5/2005
WO    2014018748 A1   1/2014
(Continued)

OTHER PUBLICATIONS

Disclosed Anonymously: "(S)-2-(2-(benzofuran-6-carbonyl)-5,7-dichloro-1,2,3,4-tetrahydroisoquinoline-6-carboxamido)-3-(3-(methylsulfonyl)phenyl) propanoic acid", i.p.com Ournal, ip.com Inccccc,West Henrietta, NY, US Aug. 29, 2017.
(Continued)

Primary Examiner — Jeffrey H Murray
(74) Attorney, Agent, or Firm — Silvia Salvadori, P.C.; Silvia Salvadori

(57) ABSTRACT

The invention relates to a process for the preparation of Lifitegrast of formula (I), which comprises: a) condensation of the compound of formula (II) with the compound of formula (III) to give the compound of formula (IV) wherein $R_1$, $R_2$ and $R_3$ are independently selected from straight or branched $C_1$-$C_6$ alkyl groups; b) chlorination of compound (IV) in the presence of a chlorinating agent (IV), (V), c) condensation of compound (V) with amino acid (VI) to give compound (I), c) condensation of compound (V) with amino acid (VI) to give compound (I), d) optional purification of the crude Lifitegrast in mixtures of polar aprotic solvents and water.

(Continued)

-continued

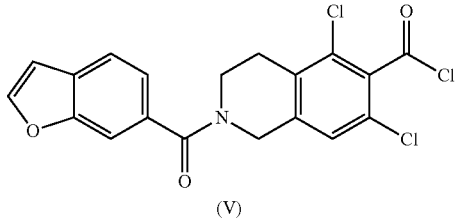

(V)

-continued

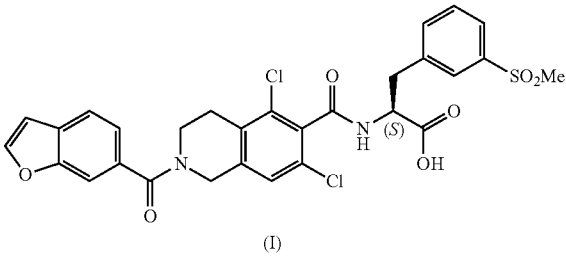

(I)

15 Claims, 1 Drawing Sheet (V) +  Cl⁻

(VI)

(58) Field of Classification Search
USPC .......................................... 546/146; 514/307
See application file for complete search history.

(56) References Cited

FOREIGN PATENT DOCUMENTS

| WO | 2019004936 A1 | 1/2019 | |
|---|---|---|---|
| WO | WO2019/004936 | * 1/2019 | ........... C07D 405/06 |
| WO | 2019026014 A1 | 2/2019 | |
| WO | 2019043724 A1 | 3/2019 | |

OTHER PUBLICATIONS

Flick A.C., et al., "Synthetic approaches to new drugs approved during 2016", Journal of Medicinal Chemistry, vol. 61, No. 16, Apr. 5, 2018, pp. 7004-7031.
Search Report and Written Opinion of PCT/IB2019/054943 dated Aug. 23, 2019.

* cited by examiner

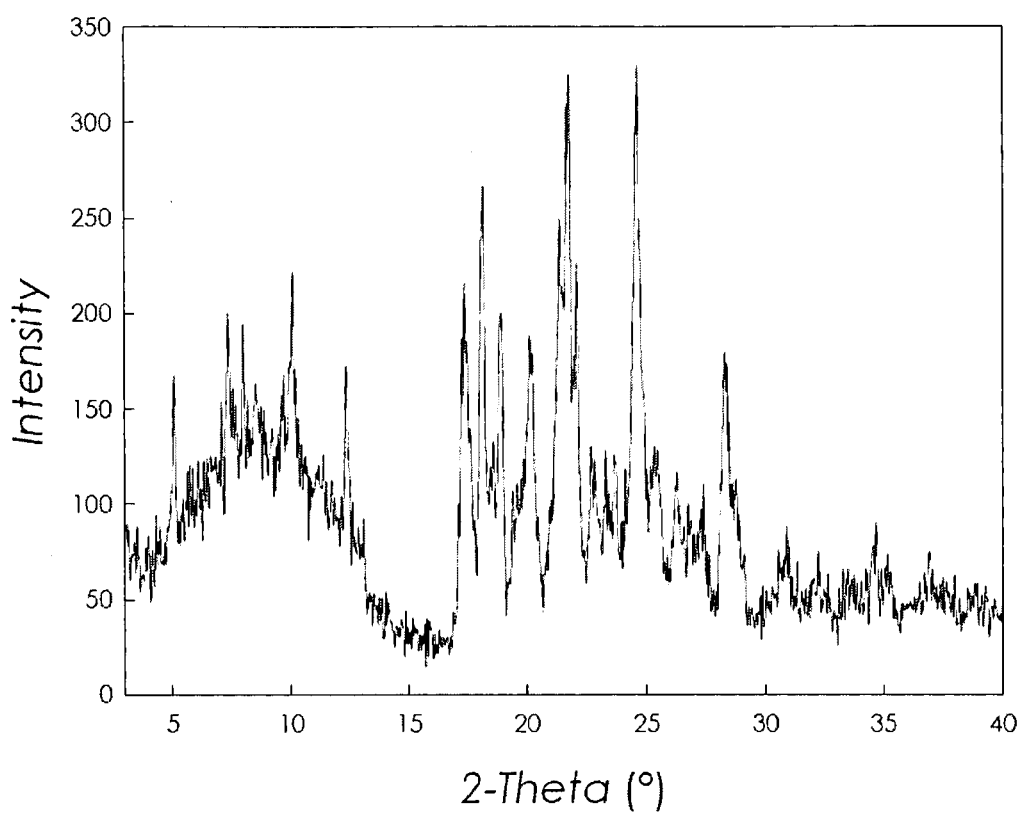

PROCESS FOR THE PREPARATION OF LIFITEGRAST

This application is a U.S. national stage of PCT/IB2019/054943 filed on 13 Jun. 2019, which claims priority to and the benefit of Italian Application No. 102018000006337 filed on 14 Jun. 2018, the contents of which are incorporated herein by reference in their entireties.

The present invention relates to a process for the preparation of Lifitegrast, the international non-proprietary name of which is N-[[2-(6-benzofuranylcarbonyl)-5,7-dichloro-1,2,3,4-tetrahydro-6-isoquinolinyl]carbonyl]-3-(methylsulphonyl)-L-phenylalanine, having the formula (I):

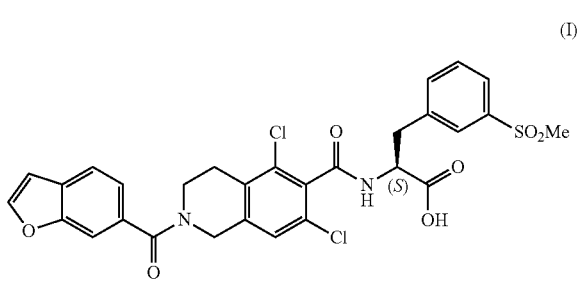

Technical Context

Lifitegrast, used for the treatment of keratoconjunctivitis sicca (KCS), also known as dry eye syndrome, is described in WO2005044817 (SARcode Bioscience Inc).

Lifitegrast bonds to integrin LFA-1, a cell-surface protein found on the leucocytes, which blocks their interaction with the intercellular adhesion molecules (ICAM-1), which play an important part in inflammation of the eye surface.

A number of synthesis methods have been described, which involve a series of protections and deprotections of the acid and basic groups of the intermediates, and therefore as last step, the conversion of a Lifitegrast ester to give the desired product. Said step is very delicate because, if not controlled, it could produce the final compound with a low degree of purity. The prior art therefore sought to develop different methods of conversion from ester to acid, operating under various conditions to eliminate said drawback.

The first synthesis method disclosed in U.S. Pat. No. 7,314,938 (WO2005044817) involves, in step N-1, a condensation reaction between (S)-benzyl-2-amino-3-(3-(methylsulphonyl)phenyl)propionate methyl ester and 2-(6-benzofuranylcarbonyl)-5,7-dichloro-1,2,3,4-tetrahydro-6-isoquinoline-carboxylic acid, and the subsequent basic hydrolysis of the resulting compound to give Lifitegrast.

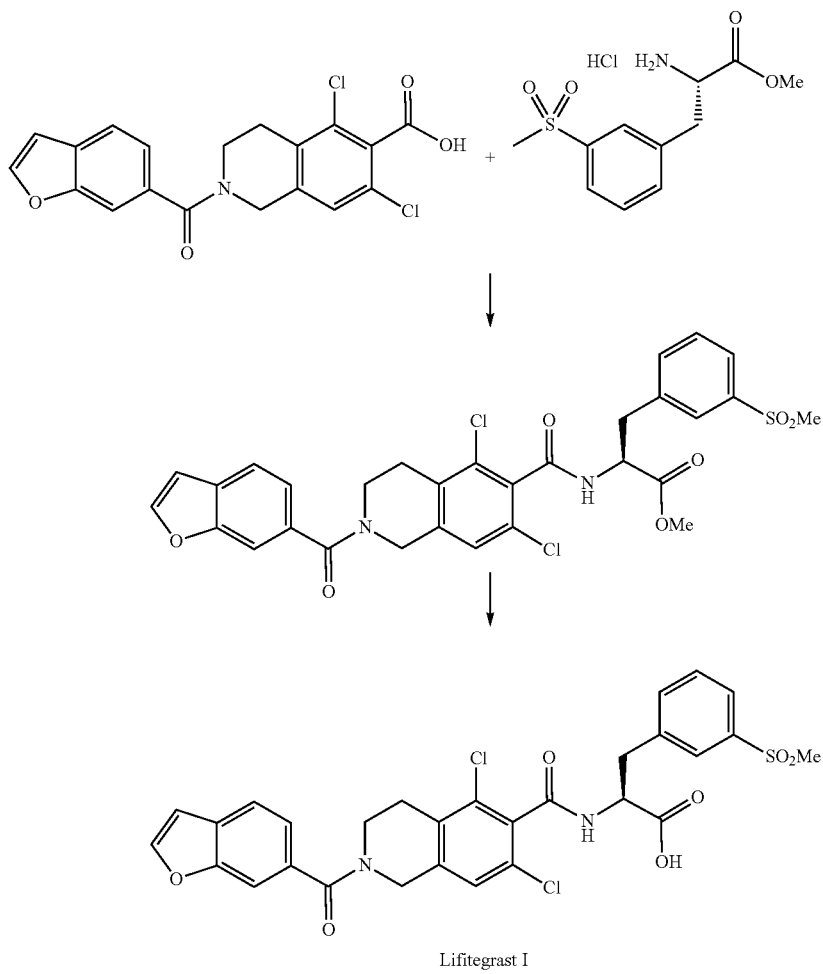

Lifitegrast I 2-(6-Benzofuranylcarbonyl)-5,7-dichloro-1,2,3,4-tetrahydro-6-isoquinoline-carboxylic acid is obtained by condensation of the amino group of 5,7-dichloro-1,2,3,4-tetrahydroquinoline-6-carboxylic acid methyl ester, previously deprotected from its tert-butoxycarbonyl protecting group, with 6-benzofurancarboxylic acid.

The last step is hydrolysis of the methyl ester to give the carboxylic acid.

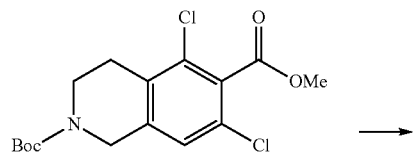

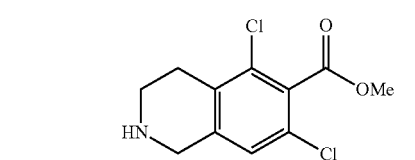

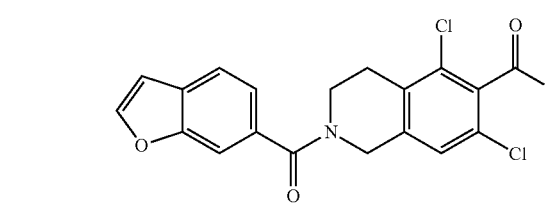

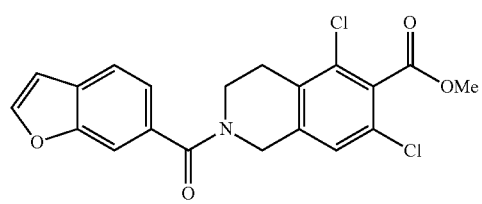

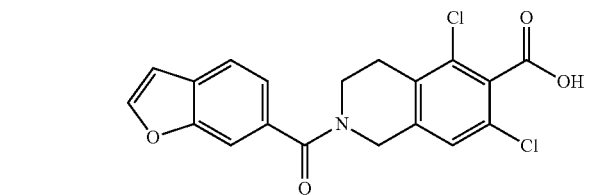

(S)-Benzyl-2-amino-3-(3-(methylsulphonyl)phenyl)propionate as hydrochloride salt is obtained from (R,R)-(−)-pseudoephedrine glycinamide by following the synthesis reported in the scheme below:

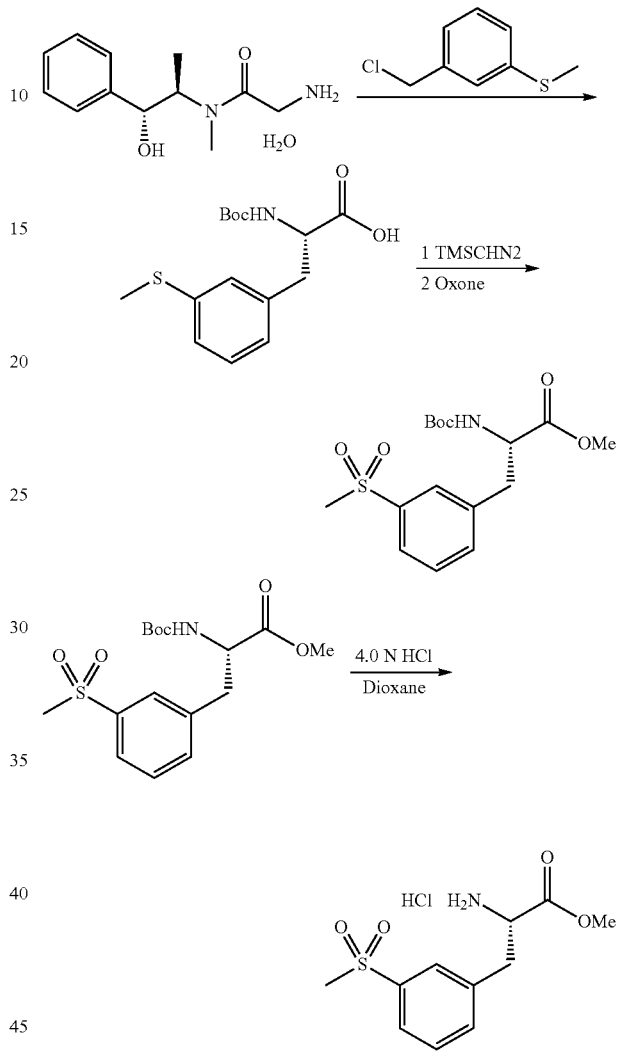

In patent application WO2009139817, the synthesis steps described above are inverted. 2-(BOC)-5,7-dichloro-1,2,3,4-tetraisoquinoline-6-carboxylic acid is condensed with benzyl (S)-benzyl-2-amino-3-(3-(methylsulphonyl)phenyl) propionate, and the amino protecting group is then removed to condense the compound with 6-benzofurancarboxylic acid acyl chloride.

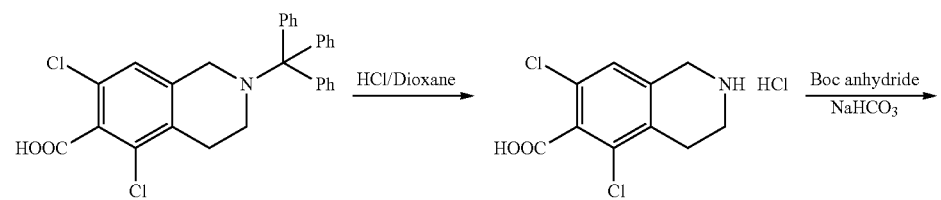

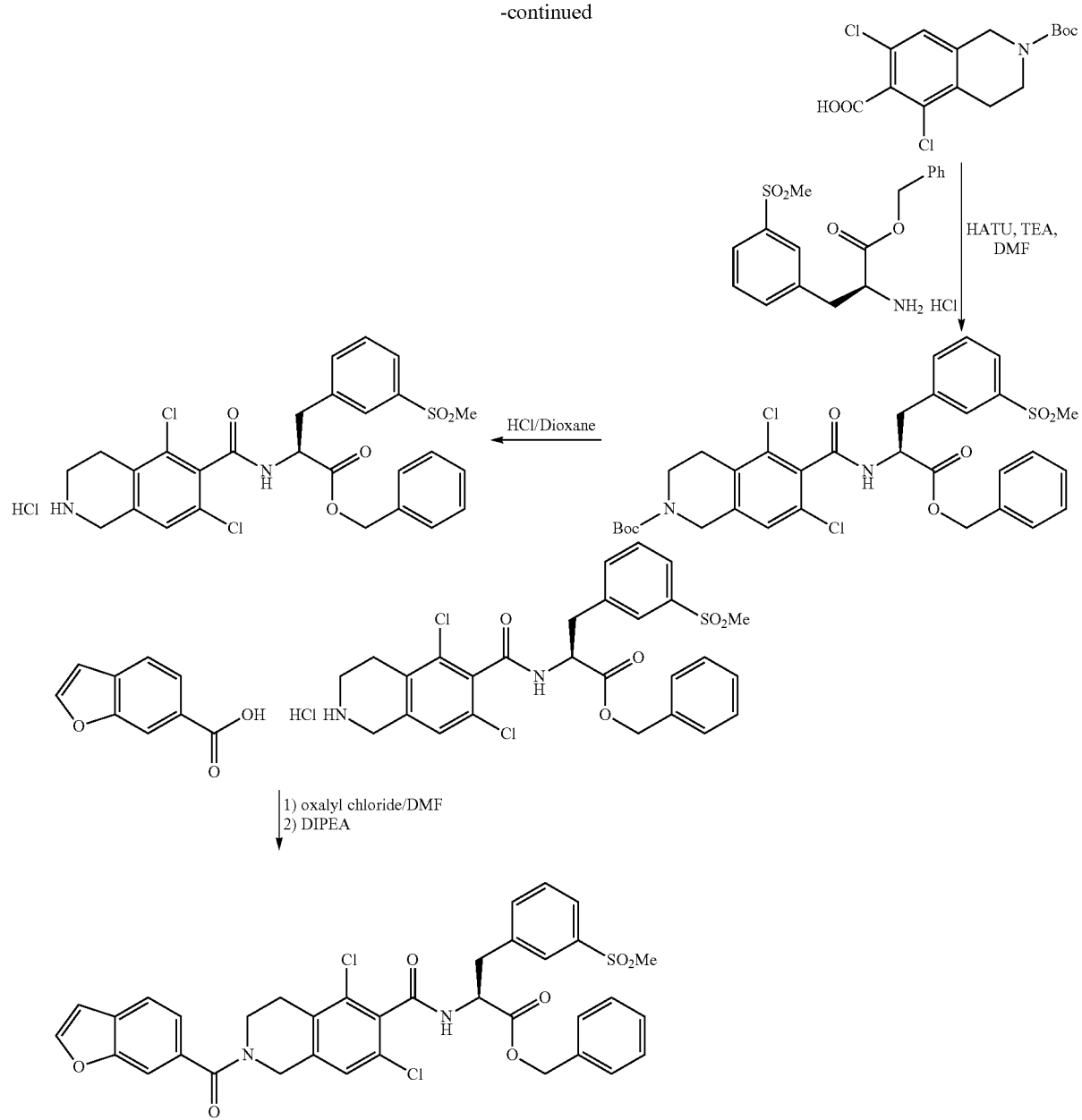
This is followed by the hydrogenation reaction of the benzyl ester, which gives rise to Lifitegrast.
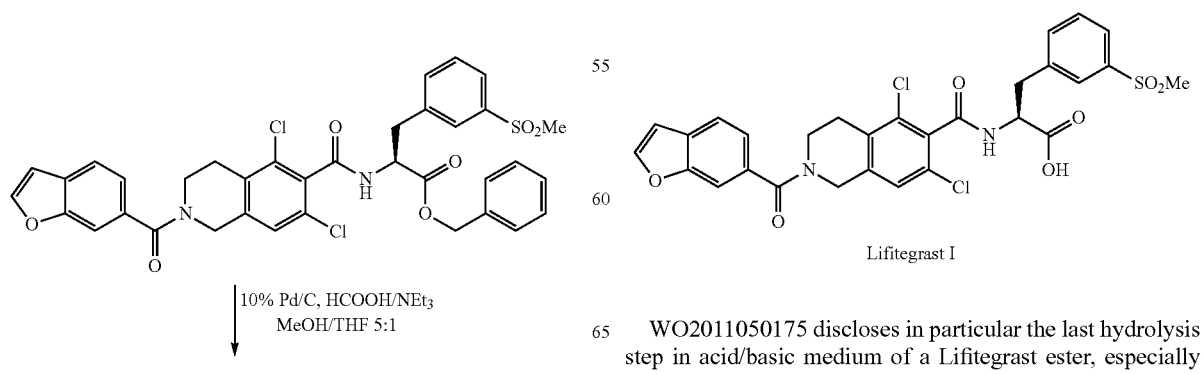
Lifitegrast I
WO2011050175 discloses in particular the last hydrolysis step in acid/basic medium of a Lifitegrast ester, especially the benzyl ester.

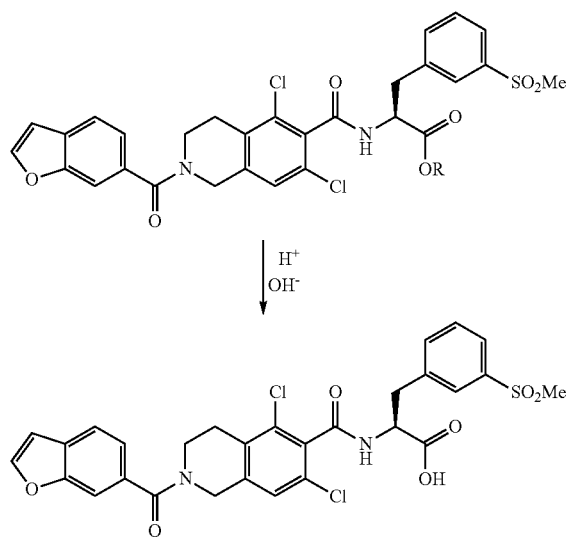

Application WO2014018748 aims to improve the final hydrolysis reaction by using, as Lifitegrast precursor esters, compounds containing silyl groups, to hydrolyse the final compound with less difficulty.

DESCRIPTION OF THE INVENTION

It has surprisingly been found that protection of the amino or acid groups during the condensation reactions of the intermediates of Lifitegrast can be avoided, therefore isolating fewer compounds and avoiding the respective protection and deprotection steps. In this way, not only is the number of steps optimised, but the sensitive final hydrolysis reaction is avoided, with the result that the pure product is obtained with good yields.

The object of the invention is therefore a process for the preparation of Lifitegrast of formula (I):

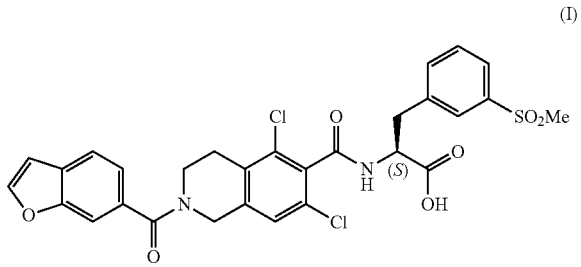

which comprises:

a) condensation of the compound of formula (II) with the compound of formula (III) to give the compound of formula (IV)

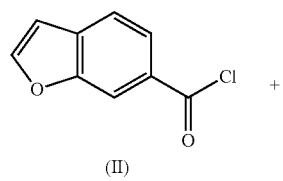

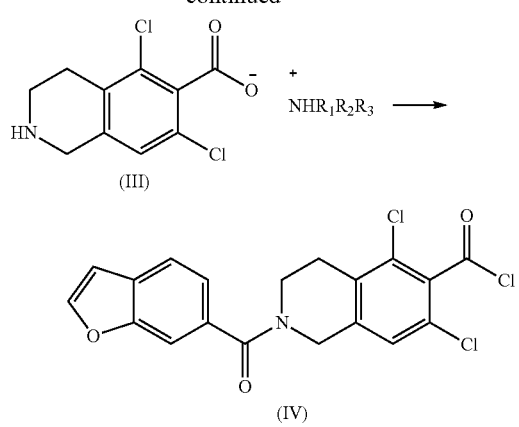

wherein $R_1$, $R_2$ and $R_3$ are independently straight or branched $C_1$-$C_6$ alkyl groups;

b) chlorination of compound (IV) in the presence of a chlorinating agent:

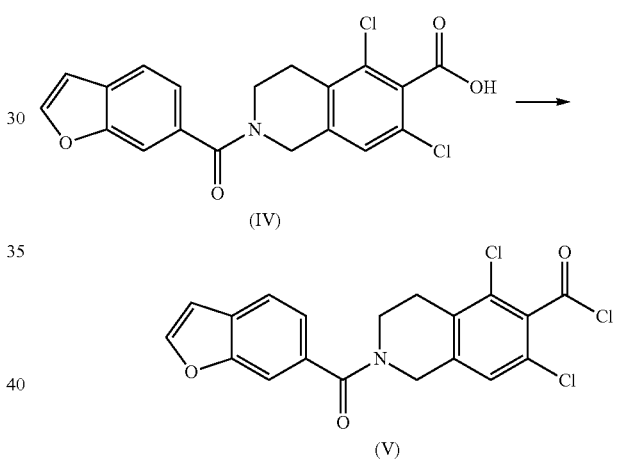

c) condensation of compound (V) with amino acid (VI) to give Lifitegrast (I)

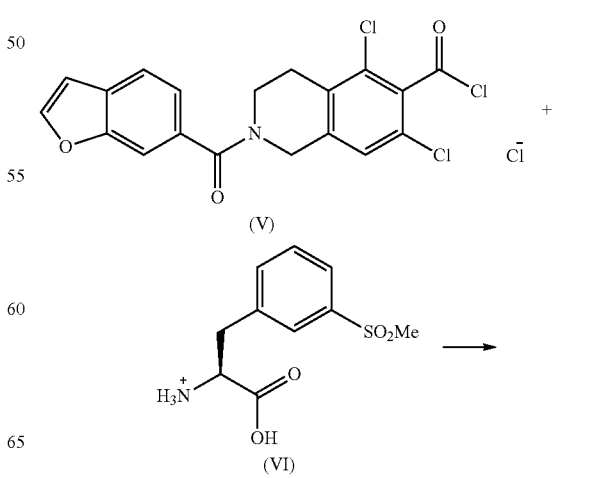

-continued

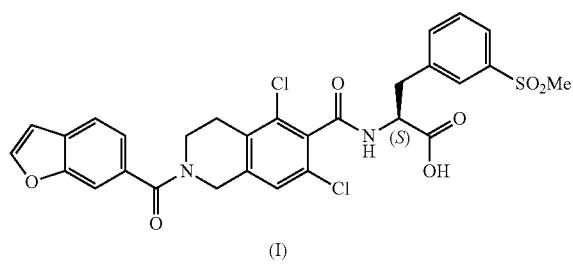

(I)

d) optional purification of crude Lifitegrast in mixtures of polar aprotic solvents and water.

Step a) is conducted in a suitable solvent, such as dimethylformamide, tetrahydrofuran, toluene or methylene chloride, preferably methylene chloride, at a temperature ranging from −10° C. to 40° C.

Step b) is conducted in a suitable solvent, such as tetrahydrofuran, toluene or methylene chloride, preferably methylene chloride, at a temperature ranging from 0° C. to 30° C. Thionyl chloride is used as chlorinating agent in the ratio of 4:1 to 1.2:1, preferably 1.5 to 1, relative to the compound of formula (IV), in the presence of catalytic amounts of dimethylformamide.

Step c) is conducted in a suitable solvent, such as dimethylformamide, tetrahydrofuran, toluene or methylene chloride, preferably methylene chloride, at a temperature ranging between −30° C. and 40° C., preferably between −10° C. and 30° C.

Step d), involving purification of crude Lifitegrast, is conducted in mixtures of polar aprotic solvents and water, preferably in a mixture of acetonitrile and water, in ratios ranging between 14:0.5 v/v and 6:1, advantageously in acetonitrile/water 10:1 v/v.

FIG. 1 shows an X-ray diffraction spectrum, measured at the Cuκα wavelength identical to that of Lifitegrast form A.

The compounds of formula (II) are obtained by reacting the acid of formula (VII) with a chlorinating agent:

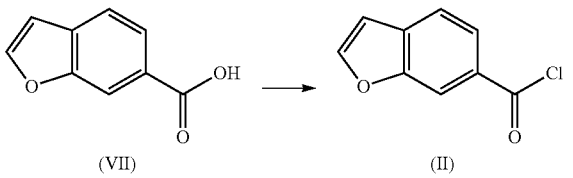 [SMILES: O=C(O)c1ccc2ccoc2c1 ; O=C(Cl)c1ccc2ccoc2c1 ; "(VII)" ; "(II)"]

The reaction takes place under conventional conditions, for example in aprotic solvents in the presence of bases and/or catalytic amounts of dimethylformamide, at a temperature ranging between 20° C. and the boiling point of the solvent. The reaction is preferably conducted in toluene at a temperature ranging between 30 and 60° C.

The compounds of formula (III) are obtained by reacting compound (VIII) with a tertiary amine $NR_1R_2R_3$ wherein groups $R_1$, $R_2$ and $R_3$, which are the same or different, are straight or branched $C_1$-$C_4$ alkyl groups. Diisopropylethylamine (DIPEA) is preferred.

The reaction is preferably conducted in polar aprotic solvents such as methylene chloride, chloroform, dimethylsulphoxide and dimethylformamide, preferably methylene chloride, at the reflux temperature of the solvent.

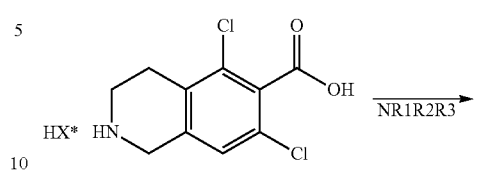

(VIII)

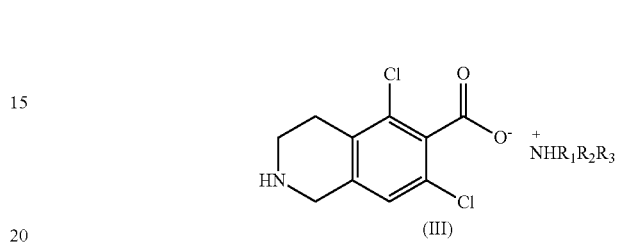

(III)

The known process for the preparation of Lifitegrast involves numerous chemical steps.

Conversely, the process according to the invention, starting with acyl chloride (II), produces Lifitegrast with a high degree of purity, in high yields and with a smaller number of steps, by eliminating the delicate final hydrolysis step present in most of the known processes.

The invention is described in detail in the examples below.

Example 1: Synthesis of Compound (II)

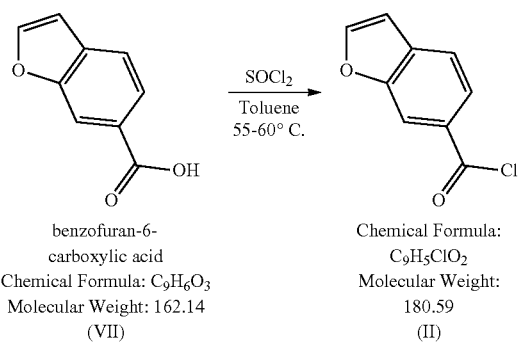 [SMILES: O=C(O)c1ccc2ccoc2c1 ; "SOCl2" ; O=C(Cl)c1ccc2ccoc2c1]

| benzofuran-6-carboxylic acid | Chemical Formula: $C_9H_5ClO_2$ |
|---|---|
| Chemical Formula: $C_9H_6O_3$ | Molecular Weight: 180.59 |
| Molecular Weight: 162.14 | (II) |
| (VII) | |

Benzofuran-6-carboxylic acid (50.0 g, 0.308 moles), toluene and a catalytic amount of dimethylformamide (DMF) are added, in sequence, to a reactor in $N_2$ atmosphere. The suspension is heated under stirring to 555° C.

$SOCl_2$ (0.370 moles) dissolved in toluene is added slowly, maintaining the temperature at 55±5° C. until conversion is complete. The solution is then concentrated under vacuum until an almost solid yellow residue is obtained.

Residue=55.6 g, molar yield=quantitative.

$^1$HNMR (300 MHz, $CDCl_3$): δ 8.32 (s, 1H), 8.01 (dd, 1H, $J_1$=8.31 Hz $J_2$=1.34 Hz), 7.87 (d, 1H, J=2.08 Hz), 7.69 (d, 1H, J=8.31 Hz), 6.88 (br d, 1H).

Example 2: Synthesis of Compound (IV)

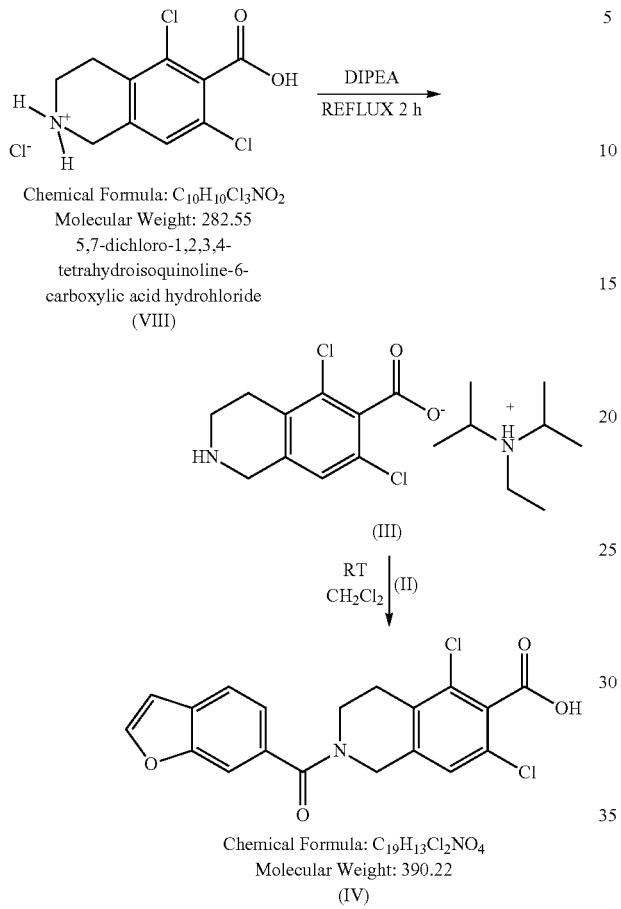

5,7-Dichloro-1,2,3,4-tetrahydroisoquinoline-6-carboxylic acid hydrochloride (30.6 g, 0.108 moles), $CH_2Cl_2$ and DIPEA are added, in sequence, to a reactor in $N_2$ atmosphere. The suspension is heated to reflux for 2 h-2 h 30 min.

The suspension is cooled to 5±5° C., and compound (II) (0.212 moles), dissolved in $CH_2Cl_2$, is dripped in slowly, maintaining the temperature.

The suspension is stirred at room temperature until completely dissolved, and left at said temperature for 16 h.

The reaction is quenched by adding dilute HCl and maintaining the temperature at 20±5° C. The resulting suspension is stirred for 1-3 h at 15-20° C., and the solid is filtered and washed with $CH_2Cl_2$ and water. The crude solid is dried under vacuum at 55-60° C. for 16-20 h.

Isolated solid=42.0 g, molar yield=99.0%.

$^1$HNMR (300 MHz, DMSO): δ 14.06 (br. s, 1H), 8.11 (d, 1H, J=2.2 Hz), 7.74 (m, 2H), 7.48 (br. s, 1H), 7.35 (d, 1H, J=8.2 Hz), 7.04 (dd, H, $J_1$=2.2 Hz $J_2$=0.8 Hz), 4.77 (br.s, 2H), 3.74 (br.s, 2H), 2.85 (t, 2H, J=5.74 Hz).

$^{13}$CNMR (75 MHz, DMSO): δ 169.91 (s), 165.98 (s), 154.13 (s), 148.14 (d), 137.86 (s), 133.70 (s), 132.64 (s), 132.11 (s), 130.38 (s), 129.11 (s), 127.45 (s), 126.45 (d), 122.49 (d), 121.86 (d), 110.81 (d), 107.28 (d), 48.92 (t), 44.33 (t), 26.89 (t) ppm.

Example 3: Synthesis of Compound (V)

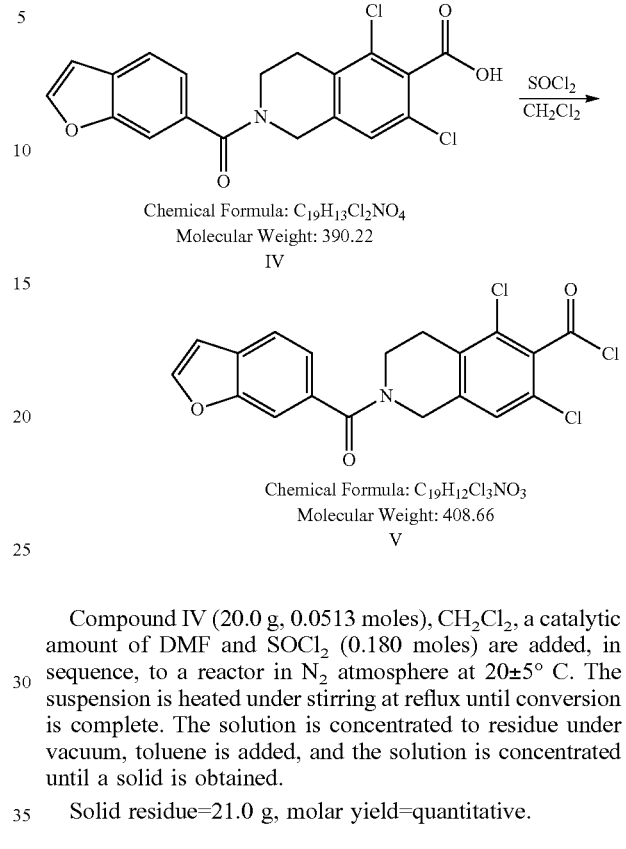

Compound IV (20.0 g, 0.0513 moles), $CH_2Cl_2$, a catalytic amount of DMF and $SOCl_2$ (0.180 moles) are added, in sequence, to a reactor in $N_2$ atmosphere at 20±5° C. The suspension is heated under stirring at reflux until conversion is complete. The solution is concentrated to residue under vacuum, toluene is added, and the solution is concentrated until a solid is obtained.

Solid residue=21.0 g, molar yield=quantitative.

Example 4: Synthesis of Compound (V)

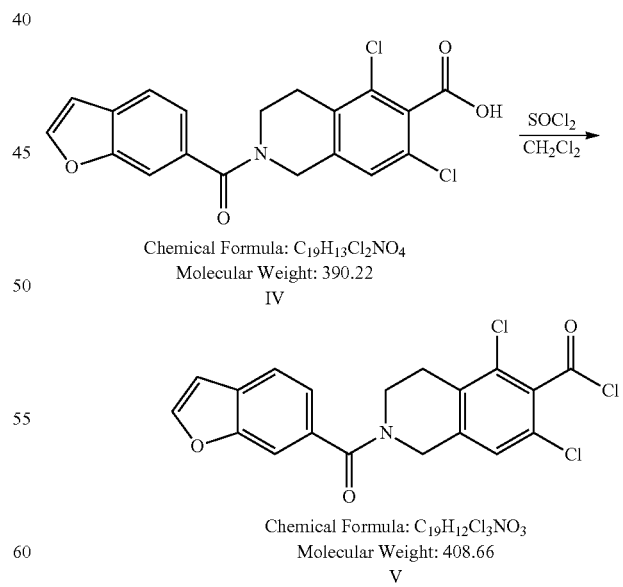

Compound IV (20.0 g, 0.0513 moles), $CH_2Cl_2$, a catalytic amount of DMF and $SOCl_2$ (0.090 moles) are added, in sequence, to a reactor in $N_2$ atmosphere at 20±5° C. The suspension is heated under stirring at reflux until conversion is complete. The solution is concentrated to residue under vacuum, toluene is added, and the solution is concentrated until a solid is obtained.

Solid residue=21.0 g, molar yield=quantitative.

Example 5: Synthesis of Lifitegrast (I)

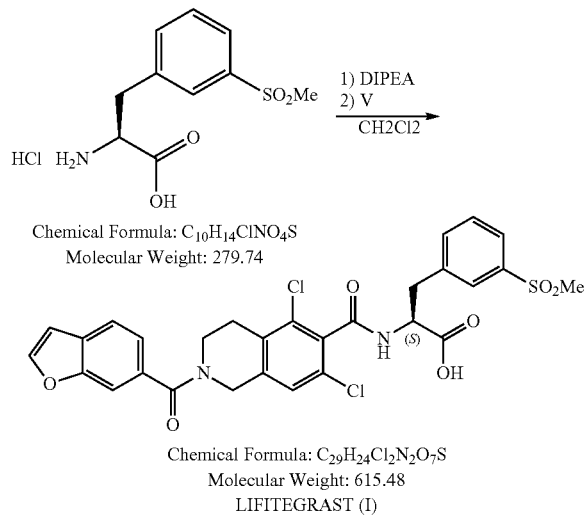

(S)-2-Amino-3-(3-(methylsulphonyl)phenyl)propanoic acid hydrochloride (0.0685 moles) and $CH_2Cl_2$ are added, in sequence, to a reactor in $N_2$ atmosphere at 20±5° C. DIPEA is added slowly to the mixture under stirring. The mixture is cooled, and compound V (20.0 g, 0.0489 moles), dissolved in $CH_2Cl_2$, is added slowly, maintaining the reaction temperature at 0-5° C. The reaction is left under stirring for 1 h 30 min-2 h at 0-5° C., and MeOH is then added. The mixture is heated to 305° C. and then cooled to 20±5° C. Dilute HCl is added. The phases are separated, and the organic phase is washed with water (2×120 mL). The organic phase is concentrated under vacuum to a constant weight.

Crude solid isolated=34.0 g, molar yield=quantitative.

Crude Lifitegrast (34.0 g) in $CH_2Cl_2$ is dissolved in a reactor in $N_2$ atmosphere. Silica gel is added, and the suspension is concentrated under vacuum until a residue is obtained. 80 vol of a 99.0% AcOEt-AcOH mixture is added, and the suspension is stirred at 20±5° C. for 30 min-1 h. The silica is filtered and washed with 5 vol of a 99.0% AcOEt-AcOH mixture. The solution is concentrated under vacuum until a foam is obtained.

Methyl ethyl ketone (165 mL) is added to the foam and, maintaining the solution under stirring at 20±5° C., a primer is added. The suspension is left under stirring at 20±5° C. for 12-16 h. The solid is filtered and washed with methyl ethyl ketone.

The solid is dried at 40-45° C. to a constant weight.

The crude solid is treated at reflux in methyl ethyl ketone (7 vol) for 1 h-1 h 30 min. The suspension is cooled to 20±5° C. and filtered after 4-8 hours. The solid is washed with methyl ethyl ketone.

The final isolated solid is dried at 40-45° C. to a constant weight.

Isolated solid=23.2 g, molar yield=77.0%.

The resulting product presents an X-ray diffraction spectrum, measured at the CuKα wavelength (FIG. 1), identical to that of Lifitegrast form A reported in U.S. Pat. No. 8,367,701 (FIG. 5, p. 5).

$^1$HNMR (300 MHz, DMSO): δ 12.87 (br. s, 1H), 9.02 (d, 1H, J=8.3 Hz), 8.12 (d, 1H, J=2.2 Hz), 7.88 (br. s, 1H), 7.79-7.55 (m, 5H), 7.49-7.32 (br. m, 2H), 7.05 (dd, 1H, $J_1$=2.2 Hz $J_2$=0.9 Hz), 4.80 (br.m, 3H), 3.71 (br.s, 2H), 3.31 (dd, 1H, J=14.0 Hz J2=4.5 Hz), 3.16 (s, 3H), 3.04 (dd, 1H, $J_1$=14.0 Hz J2=10.4 Hz), 2.78 (br.s, 2H) ppm.

$^{13}$CNMR (75 MHz, DMSO): δ 172.5 (s), 169.89 (s), 164.02 (s), 154.12 (s), 148.18 (d), 141.13 (s), 139.56 (s), 137.51 (s), 135.01 (s), 134.91 (d), 132.14 (s), 132.08 (s), 131.62 (s), 129.71 (d), 129.14 (s), 128.87 (s), 128.19 (d), 126.18 (d), 125.51 (d), 122.47 (d), 121.89 (d), 110.78 (d), 107.30 (d), 53.52 (d), 44.70 (t), 44.09 (q), 36.84 (t), 36.32 (t), 26.89 (t) ppm.

Example 6: Synthesis of Lifitegrast (I)

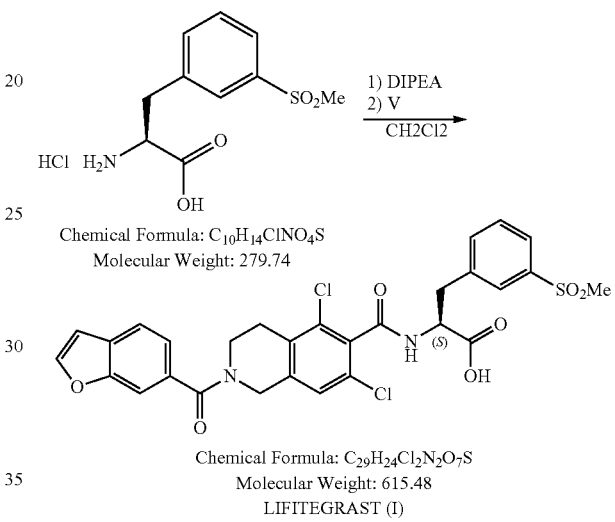

(S)-2-Amino-3-(3-(methylsulphonyl)phenyl)propanoic acid hydrochloride (0.0587 moles) and $CH_2Cl_2$ are added, in sequence, to a reactor in $N_2$ atmosphere at 20±5° C. Compound V (20.0 g, 0.0489 moles), dissolved in $CH_2Cl_2$, is added, maintaining the reaction temperature at 20±5° C. The solution is left under stirring for 5-10 min. and cooled to −5±5° C. A solution of DIPEA in $CH_2Cl_2$ is added, and maintained at −5±5° C. for 5-6 hours. Dilute HCl is added. The phases are separated at 20±5° C., and water is added. The mixture is stirred overnight at 20±5° C., and the solid is filtered. The panel is washed with $CH_2Cl_2$ and $H_2O$. The panel is dried at 50° C. under vacuum to a constant weight.

Crude solid isolated=27.7 g, molar yield=92.0%.

Crude Lifitegrast (27.7 g) and a 14:1 v/v $CH_3CN/H_2O$ mixture (5 volumes) are added, in sequence, to a reactor in $N_2$ atmosphere at 205° C. The mixture is dissolved under stirring at 75±5° C. The mixture is cooled to 20-25° C. in 1-2 h, and maintained under stirring for 20-24 h at 20-25° C. The suspension is filtered and washed with $H_2O$ (50 g) and $CH_3CN$ (2×30 g). The wet solid is dissolved in a 10:1 v/v $CH_3CN/H_2O$ mixture (4 volumes of the estimated dry matter). The mixture is dissolved under stirring at 75±5° C. with decolourising charcoal, and maintained for 30-40 min. The solution is filtered and washed with 1 volume of mixture. The mixture is cooled to 20-25° C. in 1-2 h, and maintained under stirring for 20-24 h at 20-25° C. The suspension is filtered and washed with $H_2O$ (2×30 g).

Crude solid isolated=21.6 g, molar yield=76.0%.

Example 7: Crystallisation of Lifitegrast from CH$_3$CN/H$_2$O

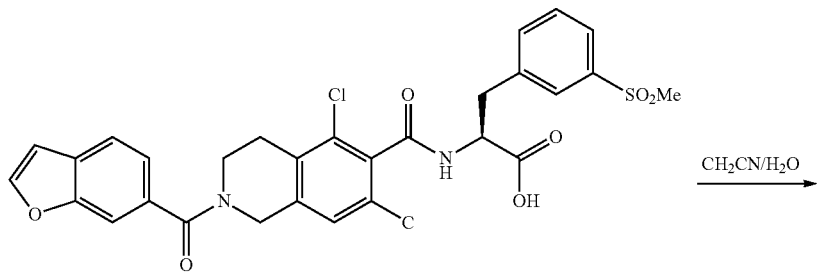

Chemical Formula: C$_{29}$H$_{24}$Cl$_2$N$_2$O$_7$S
Molecular Weight: 615.48
CRUDE LIFITEGRAST

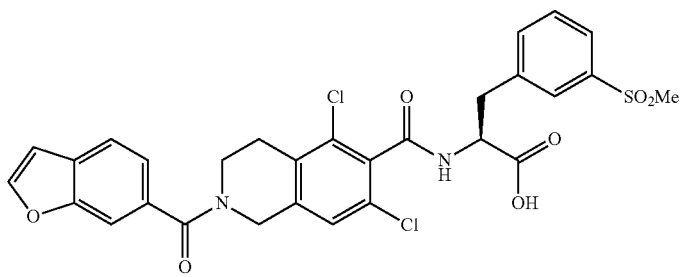

Chemical Formula: C$_{29}$H$_{24}$Cl$_2$N$_2$O$_7$S
Molecular Weight: 615.48
LIFITEGRAST Lifitegrast (317 g) and a 10:1 v/v CH$_3$CN/H$_2$O mixture (1585 mL, 5 volumes) are added, in sequence, to a reactor in N$_2$ atmosphere at 20±5° C. The mixture is dissolved under stirring at 75±5° C. The mixture is cooled to 20-25° C. in 1-2 h, and maintained under stirring for 8-12 h at 20-25° C. The suspension is filtered and the panel is washed twice with H$_2$O (2×300 g). The solid is dried under vacuum at 50-55° C. to a constant weight. Crude solid isolated=280.0 g, molar yield=88.3%.

The resulting product presents an X-ray diffraction spectrum, measured at the CuKα wavelength, identical to that of Lifitegrast form A reported in U.S. Pat. No. 8,367,701 (FIG. 5, p. 5).

The invention claimed is:

1. A process for the preparation of Lifitegrast of formula (I):

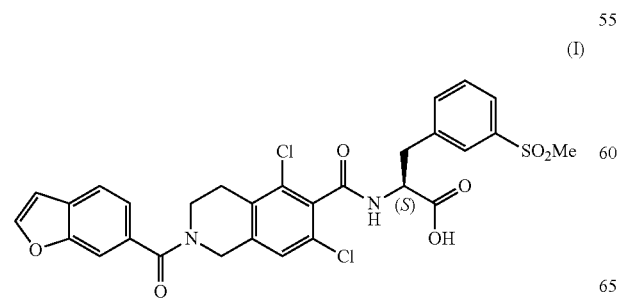

(I)

said process comprising:

a) condensating compound of formula (II) with compound of formula (III) to obtain a compound of formula (IV)

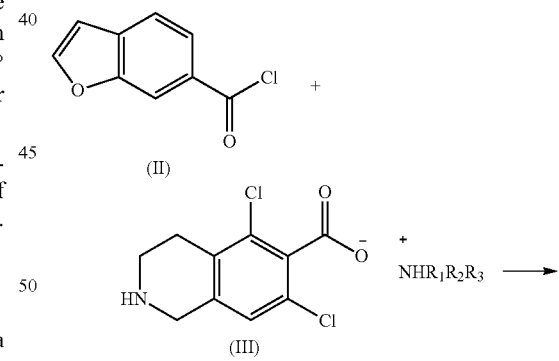

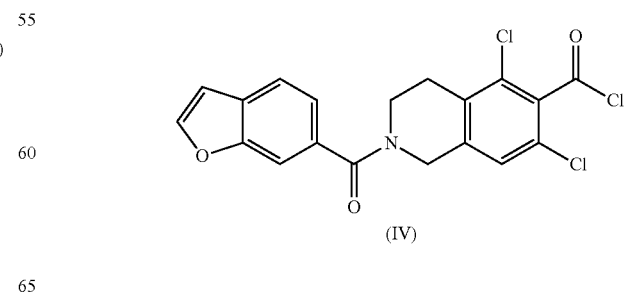

(IV)

wherein R$_1$, R$_2$ and R$_3$ are independently selected from straight or branched C$_1$-C$_6$ alkyl groups;

b) chlorinating the compound (IV) in the presence of a chlorinating agent to obtain a compound of formula (V):

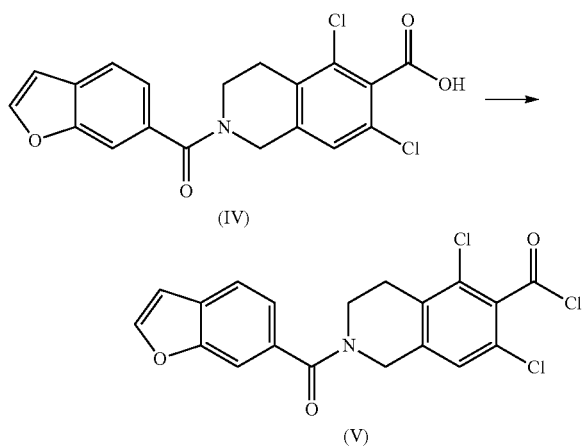

c) condensating compound (V) with amino acid (VI) to obtain compound (I):

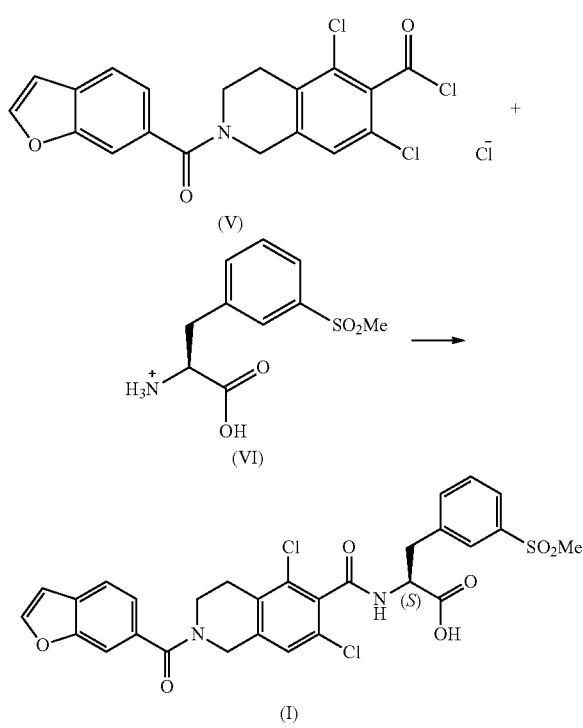

and d) crystallizing crude Lifitegrast (I) in a mixture of acetonitrile: water in a ratio of 10:1 v/v.

2. The process according to claim 1 wherein step a) is conducted in a polar aprotic solvent.

3. The process according to claim 2 wherein the solvent is methylene chloride.

4. The process according to claim 1 wherein step b) is conducted in a polar aprotic solvent, in the presence of catalytic amounts of dimethylformamide and thionyl chloride as chlorinating agent.

5. The process according to claim 4 wherein the polar aprotic solvent is methylene chloride.

6. The process according to claim 4 wherein thionyl chloride is in ratio of 4:1, relative to the compound of formula (IV).

7. The process according to claim 1 wherein step c) is conducted in a polar aprotic solvent.

8. The process according to claim 7 wherein step c) is conducted in methylene chloride at a temperature ranging between −30° C. and 40° C.

9. The process according to claim 1 wherein the compound of formula (II) is obtained by reacting the corresponding acid of formula (VII) with a chlorinating agent:

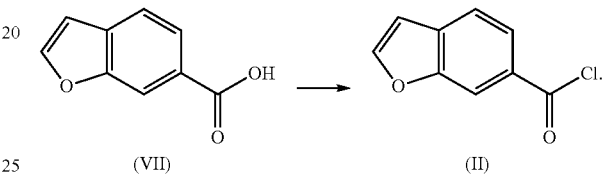

10. The process according to claim 9 wherein the reaction is conducted in apolar aprotic solvents, and the chlorinating agent is thionyl chloride.

11. The process according to claim 10 wherein the reaction is conducted in toluene.

12. The process according to claim 1 wherein compound (III) is obtained by reacting compound (VIII) with a tertiary amine $NR_1R_2R_3$ wherein groups $R_1$, $R_2$ and $R_3$, which can be the same or different, are straight or branched $C_1$-$C_4$ alkyl groups

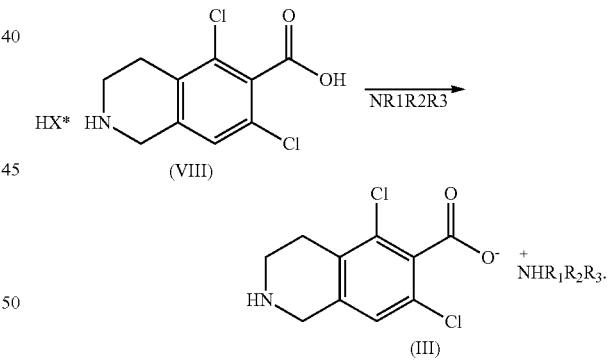

13. The process according to claim 12 wherein the tertiary amine is diisopropylethylamine.

14. The process according to claim 4 wherein thionyl chloride is in ratio 1.5:1 relative to the compound of formula (IV).

15. The process according to claim 7 wherein step c) is conducted in methylene chloride at a temperature ranging between −10° C. and 30° C.

* * * * *